United States Patent
Wood et al.

(10) Patent No.: US 8,961,787 B2
(45) Date of Patent: Feb. 24, 2015

(54) SYSTEMS AND METHODS FOR PROCESSING COMPLEX BIOLOGICAL MATERIALS

(75) Inventors: Nichole Lea Wood, Niskayuna, NY (US); Reginald Donovan Smith, Schenectady, NY (US); Hongyi Zhou, Niskayuna, NY (US); Liming Yu, Clifton Park, NY (US); Brian Polizzotti, Clifton Park, NY (US); Peter Miller, New London, CT (US)

(73) Assignee: General Electric Company, Niskayuna, NY (US)

( * ) Notice: Subject to any disclaimer, the term of this patent is extended or adjusted under 35 U.S.C. 154(b) by 285 days.

(21) Appl. No.: 12/325,672

(22) Filed: Dec. 1, 2008

(65) Prior Publication Data

US 2010/0133181 A1    Jun. 3, 2010

(51) Int. Cl.
| C02F 9/00 | (2006.01) |
| B01D 63/02 | (2006.01) |
| A61M 1/02 | (2006.01) |
| B01D 61/28 | (2006.01) |
| B01D 61/30 | (2006.01) |

(52) U.S. Cl.
CPC .............. *B01D 63/02* (2013.01); *A61M 1/029* (2013.01); *B01D 61/28* (2013.01); *B01D 61/30* (2013.01)
USPC ........ 210/259; 210/143; 210/206; 210/257.1; 210/258; 210/636; 210/638

(58) Field of Classification Search
None
See application file for complete search history.

(56) References Cited

U.S. PATENT DOCUMENTS

| 4,621,231 A | 11/1986 | Heinrich et al. |
| 4,663,058 A | 5/1987 | Wells et al. |
| 5,397,479 A | 3/1995 | Kass et al. |
| 5,472,621 A | 12/1995 | Matkovich et al. |
| 5,482,829 A | 1/1996 | Kass et al. |
| 5,614,106 A | 3/1997 | Payrat et al. |
| 5,670,060 A | 9/1997 | Matkovich et al. |
| 6,027,688 A | 2/2000 | Wainwright |
| 6,444,471 B1 | 9/2002 | Johnson |
| 6,544,751 B1 | 4/2003 | Brandwein et al. |
| 2002/0179537 A1 | 12/2002 | Sukavaneshvar et al. |
| 2003/0134416 A1 | 7/2003 | Yamanishi et al. |
| 2003/0206111 A1 | 11/2003 | Gao et al. |
| 2005/0173315 A1 | 8/2005 | Bosch et al. |
| 2007/0083145 A1 | 4/2007 | Murakami et al. |

FOREIGN PATENT DOCUMENTS

| DE | 102004018347 A1 | 10/2005 |
| JP | 07507717 A | 8/1995 |

(Continued)

OTHER PUBLICATIONS

PCT/SE2009/051327 Search Report, Jan. 8, 2010.

(Continued)

*Primary Examiner* — Dirk Bass
(74) *Attorney, Agent, or Firm* — Fletcher Yoder, P.C.

(57) ABSTRACT

Method and systems, for processing biological material, that contain a biological material in a vessel; add an aggregating agent to the material in the vessel and allow the material to separate into two or more distinct submaterials; extract one or more of the submaterials from the vessel; automatically transport one or more of the submaterials remaining in the vessel to a filtration device; and collect a resulting target retentate into a target retentate receptacle.

19 Claims, 20 Drawing Sheets

(56) References Cited

FOREIGN PATENT DOCUMENTS

| JP | 08510322 A | 10/1996 |
|---|---|---|
| JP | 2005529746 A | 10/2005 |
| WO | 9325295 A1 | 12/1993 |
| WO | WO9623872 | 8/1996 |
| WO | 9629346 A1 | 9/1996 |
| WO | 2007049286 A1 | 5/2007 |
| WO | 2008133874 A1 | 11/2008 |
| WO | 2009002849 A2 | 12/2008 |

OTHER PUBLICATIONS

PCT/SE2009/051327 Written Opinion, Jan. 8, 2010.

DE102004018347 Abstract, Oct. 27, 2005.
Search Report and Written Opinion from corresponding EP Application No. 09830656.6-1456 dated Jul. 9, 2013.
Choi et al., "Continuous blood cell separation by hydrophoretic filtration", Lab on a Chip, vol. 7, No. 11, pp. 1532-1538, Nov. 1, 2007.
Carlo et al., "Equilibrium separation and filtration of particles using differential inertial focusing", Analytical Chemistry, American Chemical Society, US, vol. 80, No. 6, pp. 2204-2211, Mar. 15, 2008.
Unofficial English translation of Office Action from JP dated Aug. 20, 2013.
Xia et al., "Surface fucosylation of human cord blood cells augments binding to P-selectin and E-selectin and enhances engraftment in bone marrow", Blood, vol. 104, No. 10, pp. 3091-3096, Nov. 15, 2004.
Unofficial translation of Japanese Office Action from corresponding JP Application No. 2011-538586 dated Jun. 10, 2014.

SYSTEMS AND METHODS FOR PROCESSING COMPLEX BIOLOGICAL MATERIALS

BACKGROUND

The invention relates generally to systems and methods for processing complex biological materials into subcomponents.

Many conventional blood cell isolation procedures require preliminary red blood cell depletion and sample volume reduction. These are commonly required processing steps for long-term cell banking and regenerative medicine applications where a maximal yield of rare cells is desired in a reduced volume due to storage limitations and/or the small volume requirements needed for direct transplantation. Today, the most common techniques for processing blood-cell containing samples (e.g. cord blood, bone marrow, peripheral blood) involve density-gradient sedimentation using centrifugation with or without the use of a density-gradient media to improve separations. Automated centrifugal systems have recently been developed for closed-system processing of cord blood and bone marrow samples in order to meet the growing needs for high-throughput sample processing. While greatly improving throughput compared to manual techniques, centrifugation-based devices have limited flexibility and portability due to the weight and fixed physical dimensions of the centrifuge bucket.

Filtration techniques are also used in a number of blood cell separation applications. For example, depth filtration has been used for sometime to achieve removal of leukocytes from whole blood (e.g. for transfusion applications). However these filters are designed for maximal leukocyte depletion (via trapping of cells within the filter) and have not been designed for high cell recovery following the filtration step. In addition, membrane-based plasmapheresis is a common technique for removal and processing of plasma from whole blood. However, these techniques do not involve pre-depletion of the whole blood of red blood cells (RBC) prior to filtration and do not achieve the type of volume reduction that is needed in blood cell banking applications.

BRIEF DESCRIPTION

The invention is adapted to address the need for a functionally closed-system high throughput system and method for processing biological materials, such as whole blood, while achieving high target cell (such as stem cell) recoveries and viabilities for downstream cell therapy applications. Filtration is a commonly used technique for blood processing application including hemodialysis and plasmapheresis but has not previously been used in blood cell banking applications where there is a need to process biological materials such as whole blood in order to remove red blood cells and excess plasma to achieve a concentrated white blood cell (WBC) sample. This is due to the challenges associated with separating abundant red blood cells from less abundant white blood cells and even less abundant stem cells of similar size. One of the embodiments of the systems and methods comprises a two-step process involving an initial RBC aggregation and gravity sedimentation step for bulk erythrocyte removal, followed by a filtration step for cell concentration and removal of excess plasma.

One embodiment of the closed system for processing biological material comprises: a vessel for containing and enabling the biological material to separate into two or more distinct submaterials; an extraction device for removing at least one of the submaterials from the vessel; a filtration device; a conduit that transports one or more submaterials between the vessel and the filtration device; and a control device for at least transporting one or more of the submaterials between the vessel and the filtration device via the conduit. The system may comprise one or more receptacles for at least temporarily storing one or more filtrates, wherein at least one of the receptacles is a waste filtrate receptacle and at least one of the receptacles is a target retentate receptacle. The system may further comprise a valve along the conduit for selectively directing target retentate into the target retentate receptacle; and a valve along the conduit for selectively recirculating the waste filtrate at least partially through the conduit. A pump, in fluid communication with the conduit, may also be incorporated into the system for facilitating the transport of one or more submaterials between the vessel and the filtration device.

The vessel of the system may be adapted to separate the material into submaterials at least in part based on the relative weight of two or more submaterials. The submaterials may separate into sedimentary layers, wherein the extraction device is adapted to draw off or otherwise extract one or more of the sedimentary layers. In one embodiment, the extraction device is adapted to draw off a lowermost layer within the vessel, and in another embodiment, the extraction device may alternatively, or additionally, draw off an uppermost layer within the vessel, or one or more layers in between the lowermost and uppermost.

The system may further comprise a valve, in fluid communication with an agent receptacle, to selectively remove a determined amount of agent from the agent receptacle and introduce the determined amount of agent into the vessel. The extracting device in this example may be further adapted to draw a determined amount of material from the vessel, into which the agent has previously been introduced, into the extracting device and then return the drawn material back into the vessel, to facilitate mixing of the material with the agent. The system may further comprise a sensing device for determining a location or level of at least one of the submaterials in the vessel.

The entire system, or a portion of the system such as the transportation of one or more of the submaterials between the vessel and the filtration device, may be automated.

An example of the methods for processing biological material generally comprises: providing a biological material in a vessel; adding an aggregating agent to the material in the vessel and allowing the material to separate into two or more distinct submaterials; extracting one or more of the submaterials from the vessel; automatically transporting one or more of the submaterials remaining in the vessel to a filtration device via a conduit; and directing a resulting target retentate into a target retentate receptacle.

One example of the methods comprises processing blood samples for subsequent cryopreservation and/or direct therapeutic applications, e.g. to reduce sample volume, achieve high recovery and viability of nucleated cells, and remove the majority of red blood cells present in the starting sample.

One example of the methods enables one to isolate a white blood cell (WBC) fraction, which comprises pluripotent stem cells, from whole cord blood, bone marrow, or peripheral blood (including GCSF stimulated peripheral blood). At least one of the example methods of the invention is capable of achieving high leukocyte recoveries (>80%), >95% CD34 recovery, and high leukocyte cell viabilities (>95%), while providing flexibility in handling a broad range of starting volumes and sample types based on adjustment of filtration times and filter cartridges used.

Unlike current methods, the methods and systems of the invention enable automated processing of complex biological fluids without requiring users to purchase and use a separate centrifuge. The methods and systems of the invention are also readily adaptable to handle a range of starting volumes, to concentrate a sample to a user-specified final volume, and for use in multiplexing processes (e.g. increasing/decreasing number of samples processed/run).

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
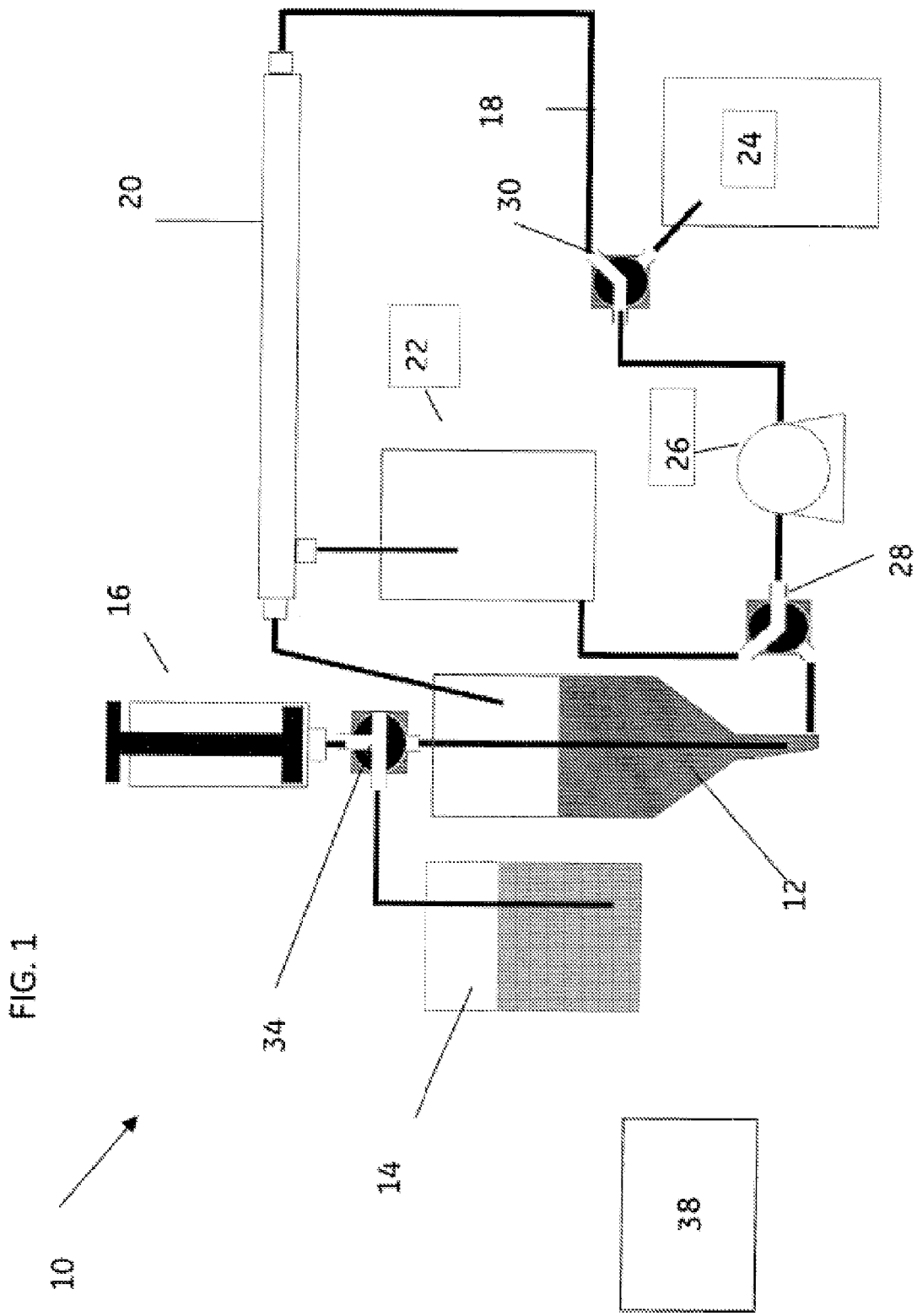
FIG. 1 is a schematic drawing of an embodiment of the system of the invention showing a biological sample and an RBC aggregating agent (w/ or w/o enhancer) in a mixing vessel and an agent receptacle, respectively.

To more clearly and concisely describe and point out the subject matter of the claimed invention, the following definitions are provided for specific terms, which are used in the following description and the appended claims. Throughout the specification, exemplification of specific terms should be considered as non-limiting examples.

As used herein, the term "vessel" refers to any object capable of containing a liquid within its confines for at least a temporary period of time having at least one port.

As used herein, the term "biological material" refers to any material of a biological nature that can be aggregated into two or more submaterials. Non-limiting examples of biological materials are whole blood, cord blood and bone marrow that can be separated via aggregation and sedimentation/removal of RBCs while nucleated cells remain in a plasma solution. Nucleated cells include WBCs and rare stem cells.

One embodiment of the methods for processing nucleated cells generally comprises the separation and enrichment of nucleated cells, such as, but not limited to, rare stem cells, from cell samples including, but not limited to, blood and bone marrow. The filtration-based embodiment comprises two general steps. The first step comprises contacting the cell sample with a settling solution, such as a red blood cell aggregating agent (e.g. Dextran) with or without the addition of an enhancing agent (e.g. sodium citrate, sodium succinate). The enhancing agent in this example embodiment is added to enhance the RBC sedimentation rate and/or reduce the final RBC packed volume following sedimentation. Subsequently the aggregated RBCs are removed from the upper fraction containing plasma and nucleated cells by drainage, drawing off or other suitable means of transfer. The second step comprises volume reduction and nucleated cell concentration by filtering the RBC-depleted sample. One example of filtration uses a hollow-fiber filtration cartridge (General Electric Healthcare, Piscataway, N.J.). This embodiment provides high cell recoveries (e.g. minimal cell trapping), minimal cell damage, and fast processing times. This example of the method is adaptable for use in the automated closed-system system. The methods and systems are adaptable for sterile processing of complex biological materials such as but not limited to cord blood and other cell sample materials.

EXAMPLE

The two-step automated example methods, that combine separation followed by filtration, rather than mere filtration, centrifugation, or magnetic separation alone, provide (1) increased total nucleated cell (TNC) recovery, (2) increased RBC removal, and (3) greater flexibility in handing a range of sample volumes (e.g. 50 to 300 mL blood) than centrifugation due to the fixed physical dimensions of the centrifuge's sample holder. Unlike a centrifuge with a fixed sized, the filters used in the systems and methods may be scaled according to the sample volume.

The volume of starting material is determined (e.g. by weight, visual inspection). The required amount of RBC aggregating reagents is calculated based on the desired stoichiometric ratio (typically 1:1 or 1:2, blood to Dextran).

The cell sample starting material is transferred to a processing vessel. The RBC aggregating reagent(s) are also transferred to the processing vessel. The sample and reagents are then mixed and allowed to incubate ~20 min for RBC aggregation and gravity sedimentation.

The aggregate RBC fraction is then extracted from the vessel from the upper white blood cell (WBC)/plasma fraction (e.g. by pumping, pipetting, or drainage). The remaining WBC/plasma fraction is then transferred (e.g. by pumping, positive or negative pressure) to a filtration device (e.g. hollow fiber cartridge) having a suitable pore size (e.g. approximately 0.65 um pores). Excess plasma passes through the filtration device and is collected in a waste filtrate receptacle, while WBCs are retained.

The fraction sample is recirculated through the filtration device until the sample volume is concentrated to the desired final volume (e.g. 5-20 ml). The sample is transferred to a target retentate receptacle, typically for longterm cryo-storage. The filter and tubing is then purged to recover cells present in this "dead volume", typically using plasma and/or air. This material is then added to the concentrated sample. High total nucleated cell recovery (>85%) and viability (>95%) are achieved.

FIG. 1 is a schematic drawing of an embodiment of the system showing a biological sample and an enhancing agent in a mixing vessel and an agent receptacle, respectively. The embodiment of the system shown and generally referred to in FIG. 1 as system 10 comprises vessel 12 for containing and enabling the biological material to separate into two or more distinct submaterials; extraction device 16 for removing at least one of the submaterials from the vessel; filtration device 20; conduit 18 that transports one or more submaterials between the vessel and the filtration device; and control device 38 for controlling at least the transporting of one or more of the submaterials between the vessel and the filtration device via the conduit. This embodiment is only an example configuration of the system. The number and type of components can be varied as needed for a given set up and the order and flow of materials through the system may be varied as well as needed. For example, the materials may be extracted, stored, flushed and mixed using various configurations and components.

In the embodiment shown in FIG. 1, vessel 12 has an opening at the top through which the extracting device, which in this example is a syringe that is in fluid communication with valve 34, introduces the agents and withdraws materials and submaterials from vessel 12 at various times during the process.

System 10 also comprises receptacles for at least temporarily storing one or more filtrates. One of the receptacles in this embodiment is waste filtrate receptacle 22 and target retentate receptacle 24. System 10 further comprises valve 30 along the conduit for selectively directing target retentate into the target retentate receptacle; valve 28 along the conduit for selectively recirculating the waste filtrate at least partially through the conduit, and valve 34 for selectively introducing one or more agents into vessel 12, extracting materials from vessel 12 to mix the agents with the sample, and extracting one or more of the submaterials from vessel 12 after aggregation of the submaterials.

System 10 may also comprise one or more sensors such as sensor 32. Sensor 32 may be used to sensing one or more parameters of the materials in vessel 12 including but not limited to the presence of a submaterial at a given location within the vessel; the environmental conditions within the vessel such as but not limited to, temperature, pH, humidity, and pressure; and qualities or characteristics of the biological materials or submaterials. The sensors may be, but are not limited to, optical sensors, ultrasonic sensors, piezoelectric sensors, motion sensors, RFID sensors, electromagnetic sensors and load sensors.

System 10 also comprises a control subsystem 38 (also referred to herein as a controller) for automating and coordinating pump 26, extraction device 16 and valves 28, 34 and 30. Control subsystem 38 may also be configured to receive input from the user of the system and automatically determine the amount and/or type of agents to be added to vessel 12 based on the amount and type of materials introduced into vessel 12 to be process using the system. The system may be fully or partially automated by the control subsystem depending on the configuration of a given system. The agents may be contained within a removable cassette that is inserted into a port in the system as needed depending on the type or amount of materials and submaterials to be processed.

System 10 further comprises pump 26, in fluid communication with the conduit, to facilitating the transport of one or more submaterials between the various components of the system. Pump 26 in this embodiment is a peristaltic pump but may comprise any type of pump suited to the configuration of the system.

Vessel 12 of the system may be adapted to separate the material into aggregated submaterials at least in part based on the relative weight of two or more submaterials. The submaterials separate into sedimentary layers and the extraction device in this embodiment is adapted to draw off or otherwise extract one or more of the sedimentary layers. In the embodiment shown in FIG. 1, extraction device 16 comprises a pick up line with a distal end located towards the bottom of vessel 12 to draw off a lowermost layer within the vessel once the submaterials have separated into their respective sedimentary layers. The extraction device may alternatively, or additionally, draw off an uppermost layer within the vessel, or one or more layers in between the lowermost and uppermost, depending on the configuration of the extraction device relative to the vessel.

Figure 2:
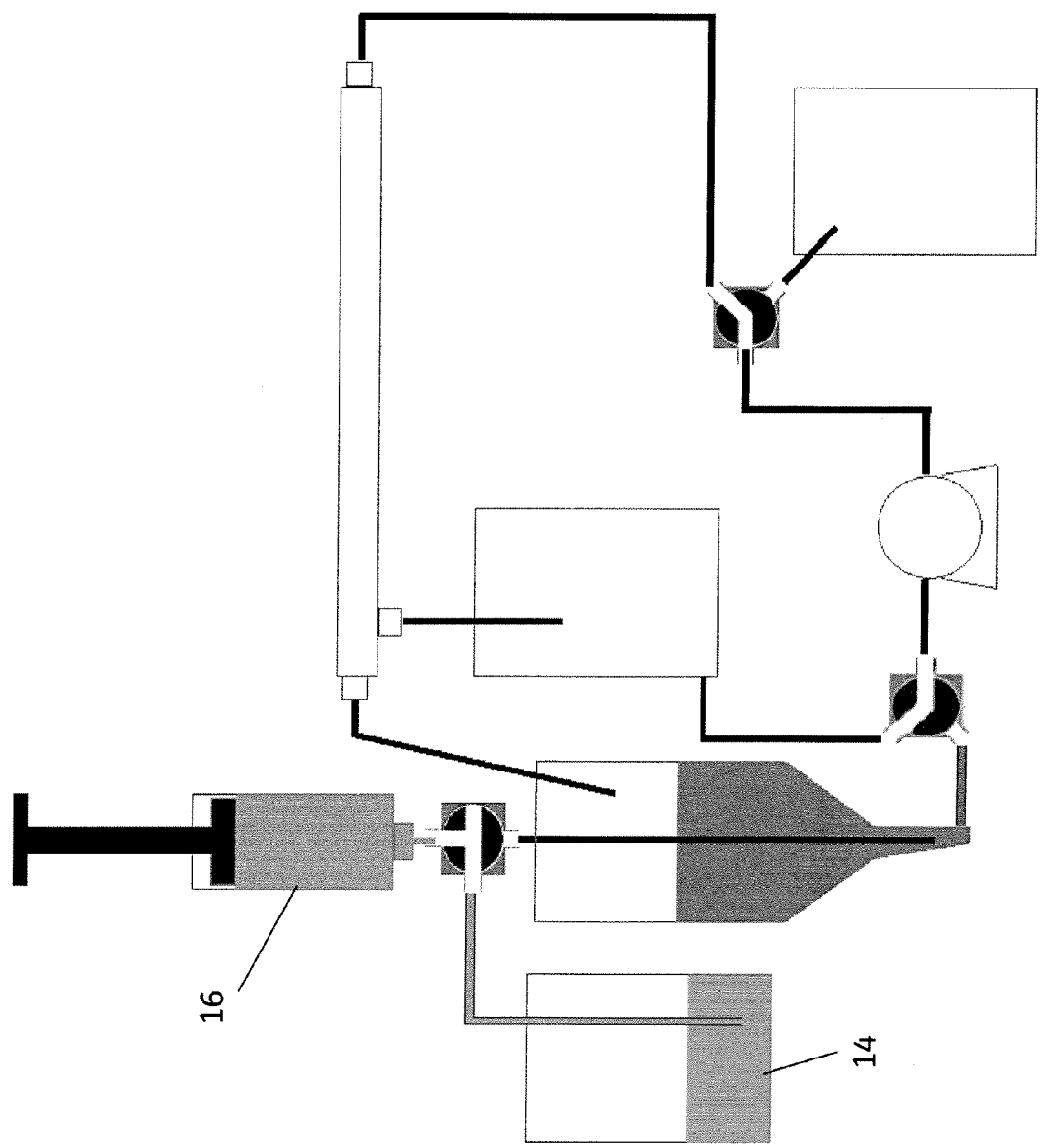
FIG. 2 is a schematic drawing of the embodiment shown in FIG. 1 showing the aggregating agent (w or w/o enhancer) drawn into an extraction device.
Figure 3:
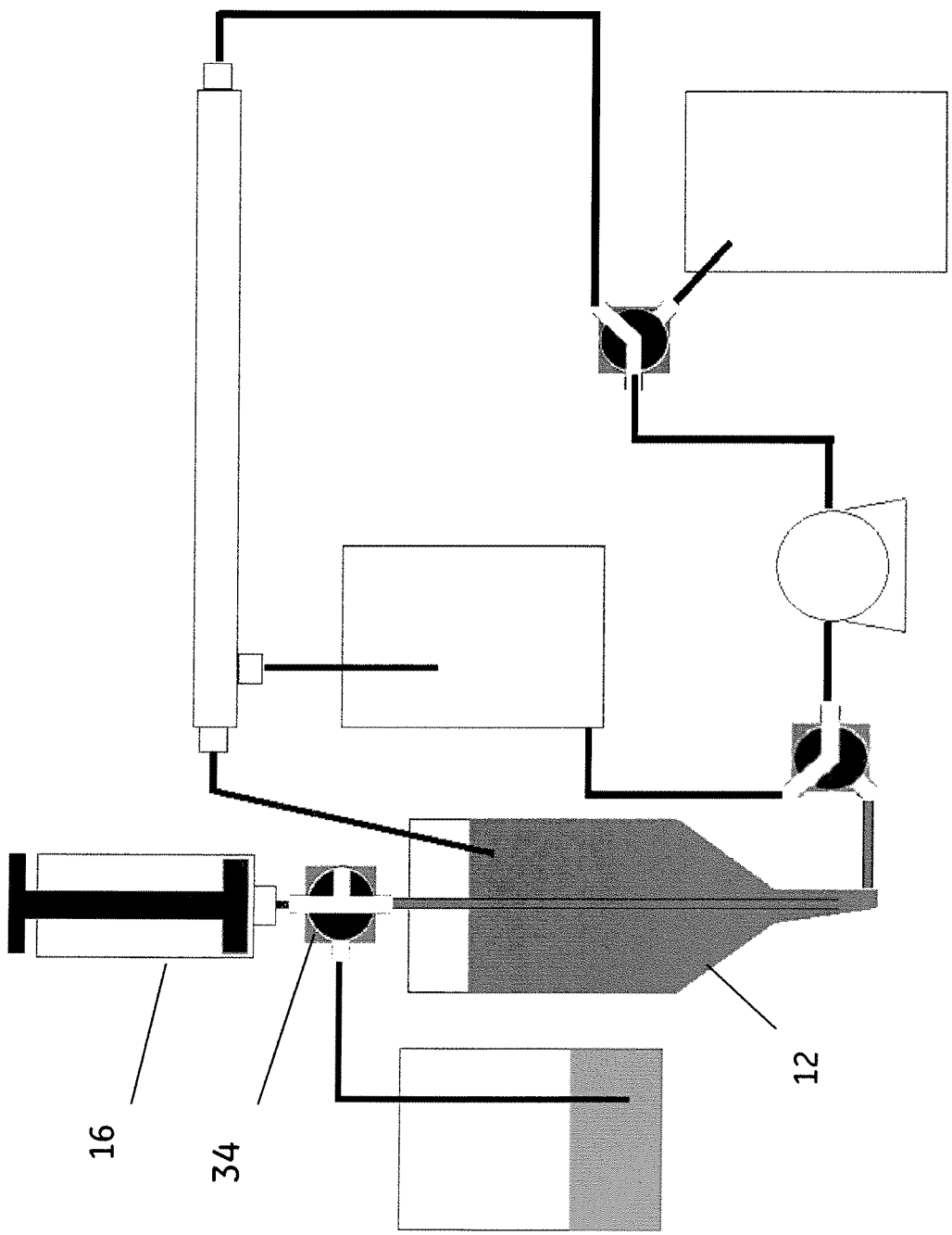
FIG. 3 is a schematic drawing of the embodiment shown in FIG. 2 showing the aggregating agent (w or w/o enhancer) agent mixed into the biological sample in the vessel.
Figure 4:
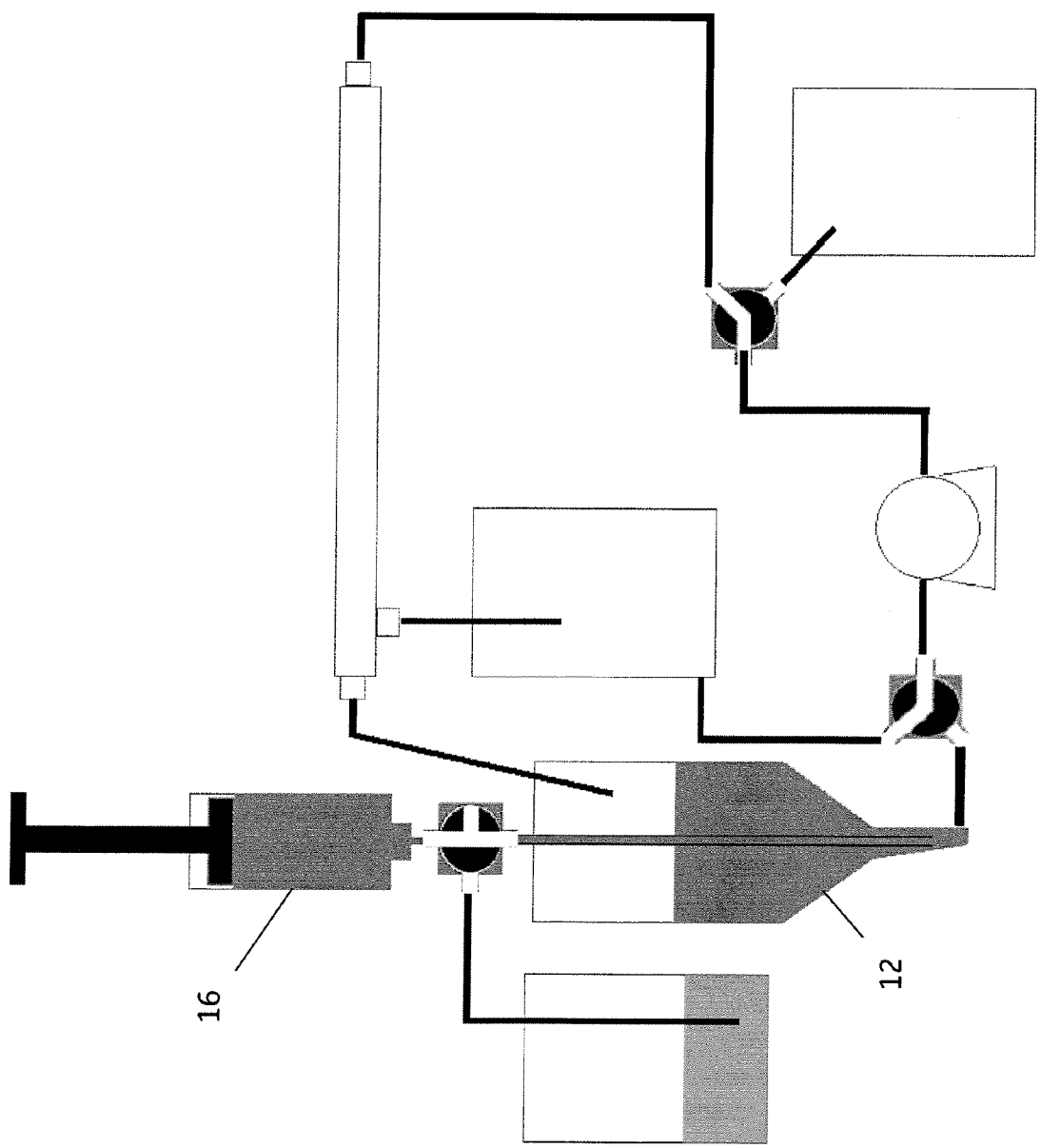
FIG. 4 is a schematic drawing of the embodiment shown in FIG. 3 showing a portion of the agent/sample mixture drawn into the extraction device.
Figure 5:
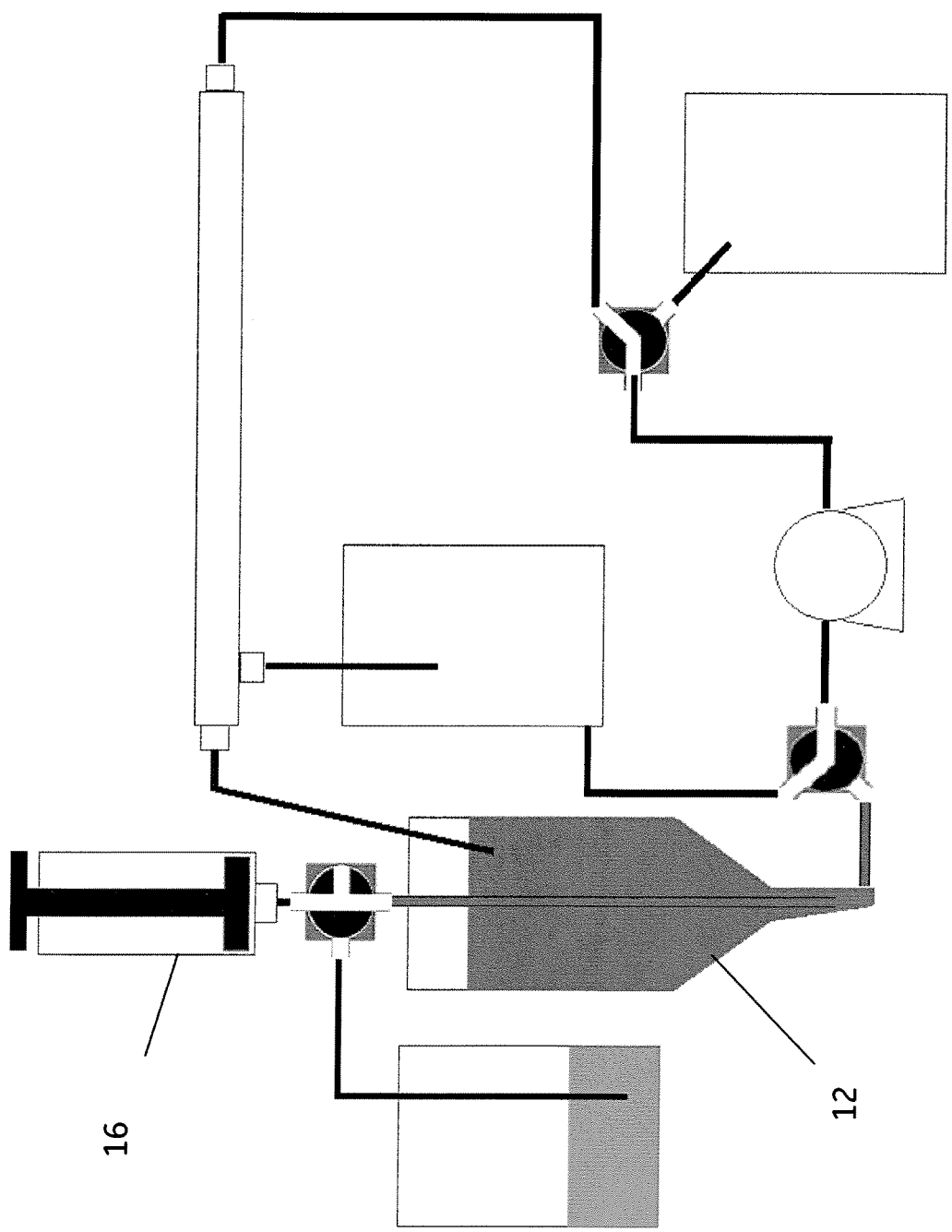
FIG. 5 is a schematic drawing of the embodiment shown in FIG. 4 showing the drawn portion returned to the vessel.

Syringe 16 together with valve 34, in fluid communication with agent receptacle 14, selectively remove a determined amount of agent from the agent receptacle and introduce the determined amount of agent into vessel 12 as shown in FIGS. 2 and 3. The extracting device in this example may be further adapted to draw a determined amount of material from the vessel, into which the agent has previously been introduced, into the extracting device and then return the drawn material back into the vessel, to facilitate mixing of the material with the agent as shown in FIGS. 4 and 5. To carry out the mixing step, valve 34 closes relative to receptacle 14 and opens relative to vessel 12 open the fluid communication between syringe 16 and vessel 12. Once the aggregating agents are mixed with the materials (e.g. whole blood) in vessel 12, the mixture typically needs time to settle into its various sedimentary layers. For whole blood or cord blood mixed, for example, with Dextran and sodium citrate, settling should occur within 20 minutes as shown in FIG. 6.

A sensing device such as sensor 32 may be used for determine when the submaterials have aggregated and separated into their respective layers by determining the location or level of at least one of the submaterials in the vessel.

Non-limiting examples of possible agents, for use in this example in which whole blood is being processed, are dextran (an aggregant), and sodium citrate and sodium succinate, which both enhance aggregation. These three examples of agents enhance the methods and systems by acting as aggregating agents and/or aggregation enhancing agents to initiate and accelerate the aggregation and sedimentation of the different types of submaterials, such as WBCs and RBCs, in the biological sample.

Figure 6:
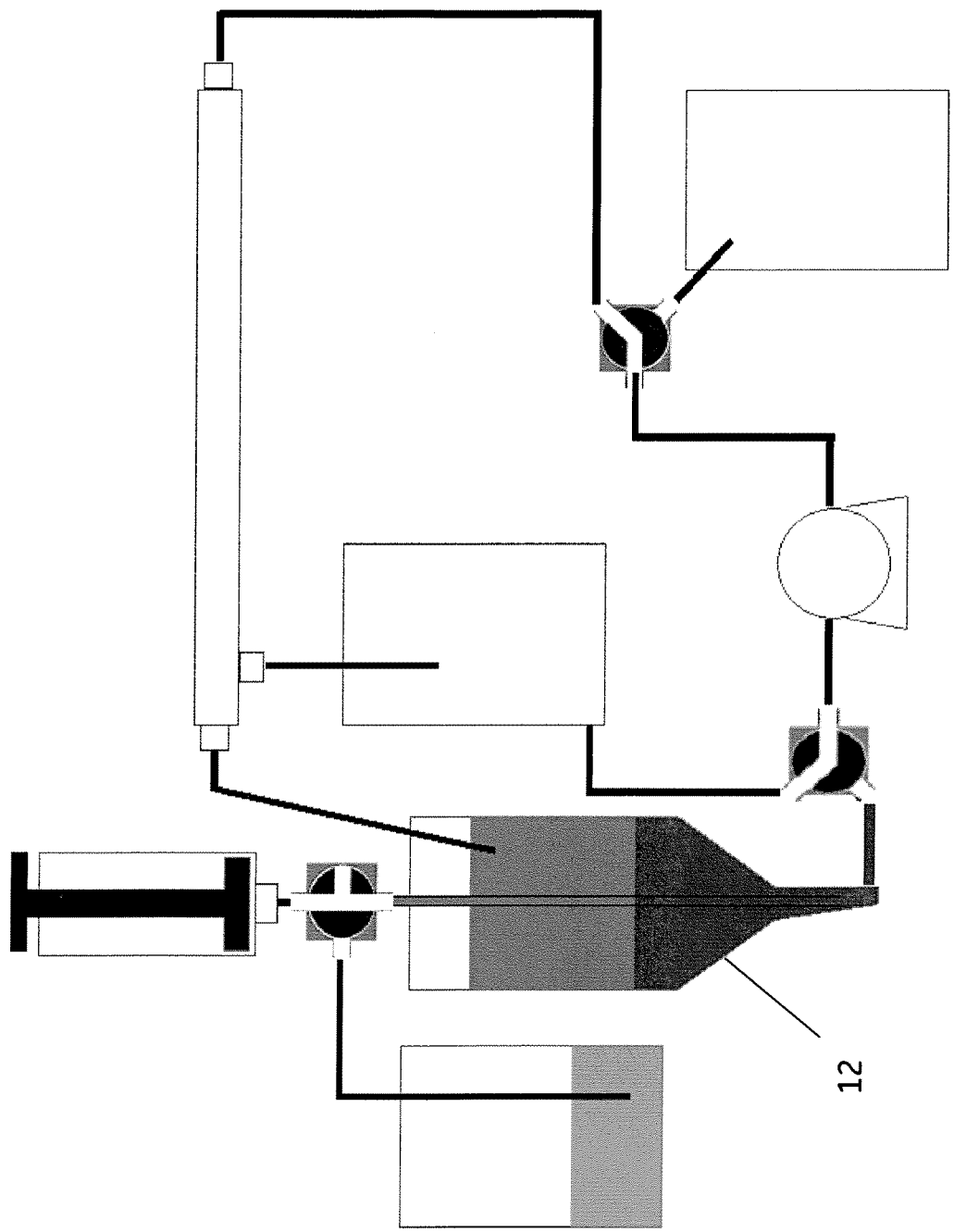
FIG. 6 is a schematic drawing of the embodiment shown in FIG. 5 showing the mixture in a state of settling.
Figure 7:
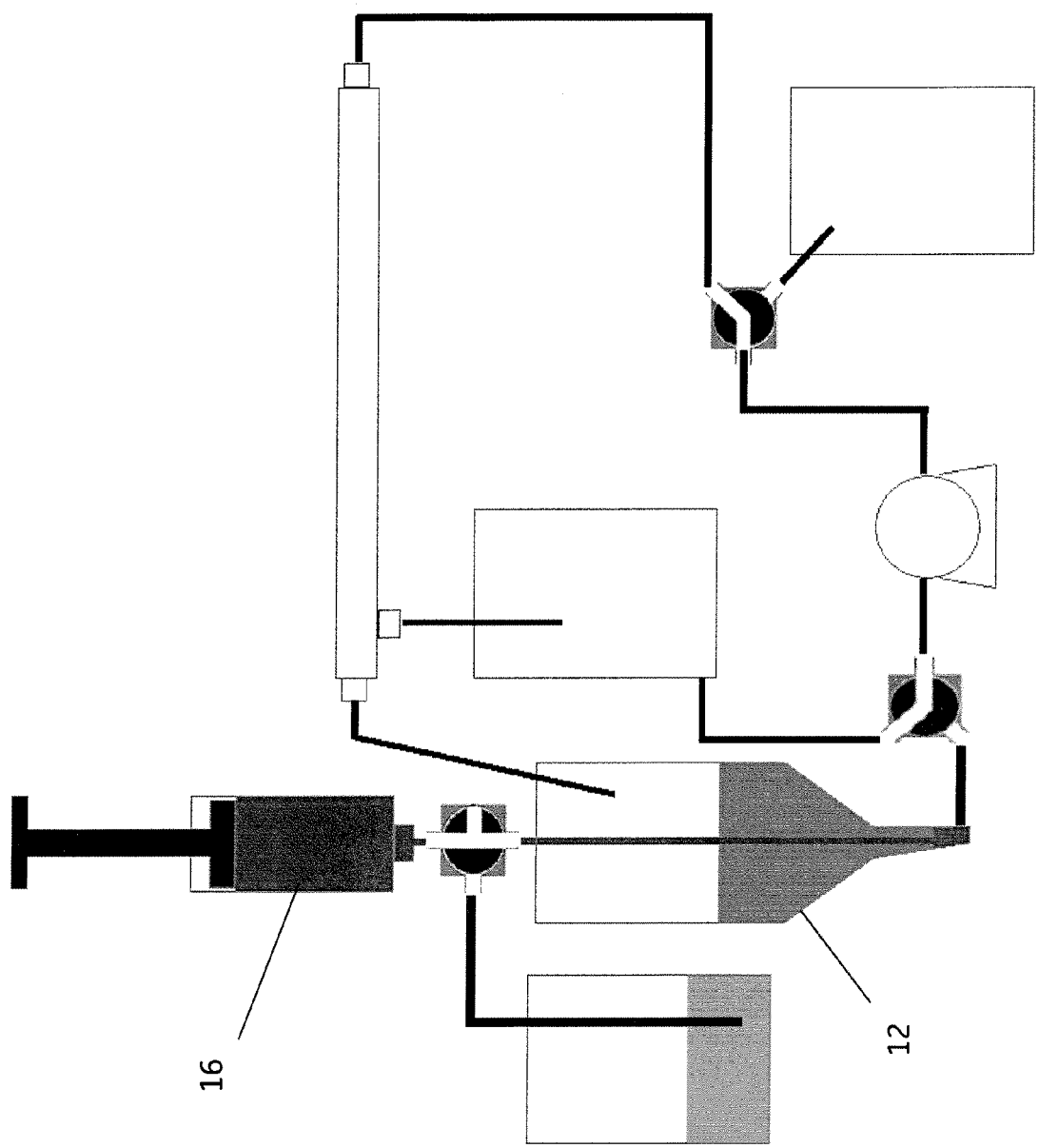
FIG. 7 is a schematic drawing of the embodiment shown in FIG. 6 showing the lowermost layer of the settled mixture drawn into the extraction device.
Figure 8:
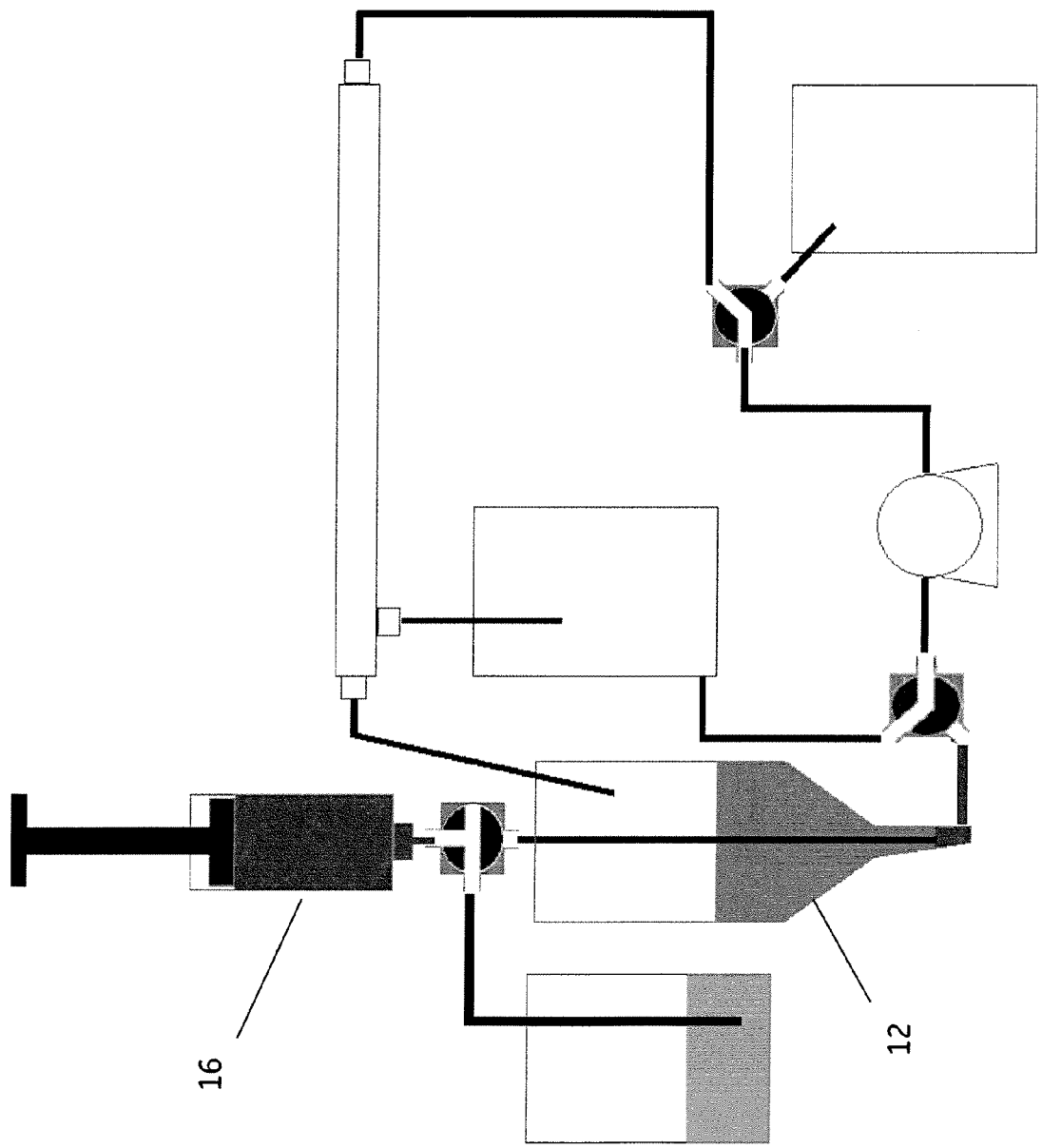
FIG. 8 is a schematic drawing of the embodiment shown in FIG. 7 showing a syringe valve between the extraction device and the vessel in a closed position.

FIG. 7 is a schematic drawing of the embodiment shown in FIG. 6 showing the lowermost layer of the settled mixture drawn into syringe 16. The system may be configured to extract one or more of the layers, such as RBCs shown in FIG. 7, until one or more of the layers reaches a predetermined set point. Sensor 32 may be used to determine when a set point is reached. Once the RBCs are withdrawn into syringe 16, valve 34 closes between syringe 16 and vessel 12 to prevent the RBCs from leaking back into the vessel. FIG. 8 is a schematic drawing of the embodiment shown in FIG. 7 showing valve 34 between the extraction device and the vessel in a closed position.

Figure 9:
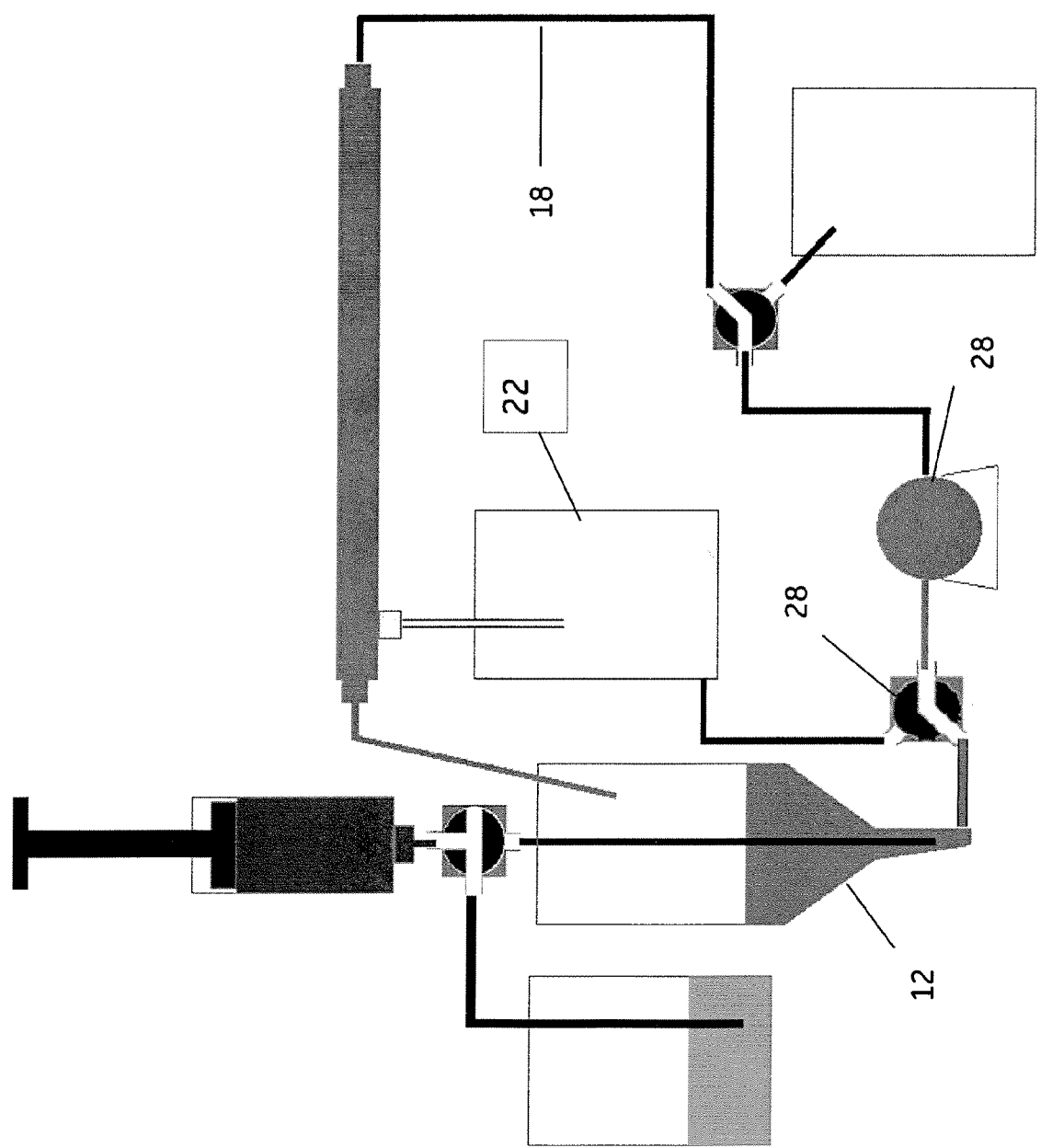
FIG. 9 is a schematic drawing of the embodiment shown in FIG. 8 showing a pump valve between the vessel and a pump in an open position and the mixture flowing through the system from the vessel through a conduit to a filtration device.
Figure 10:
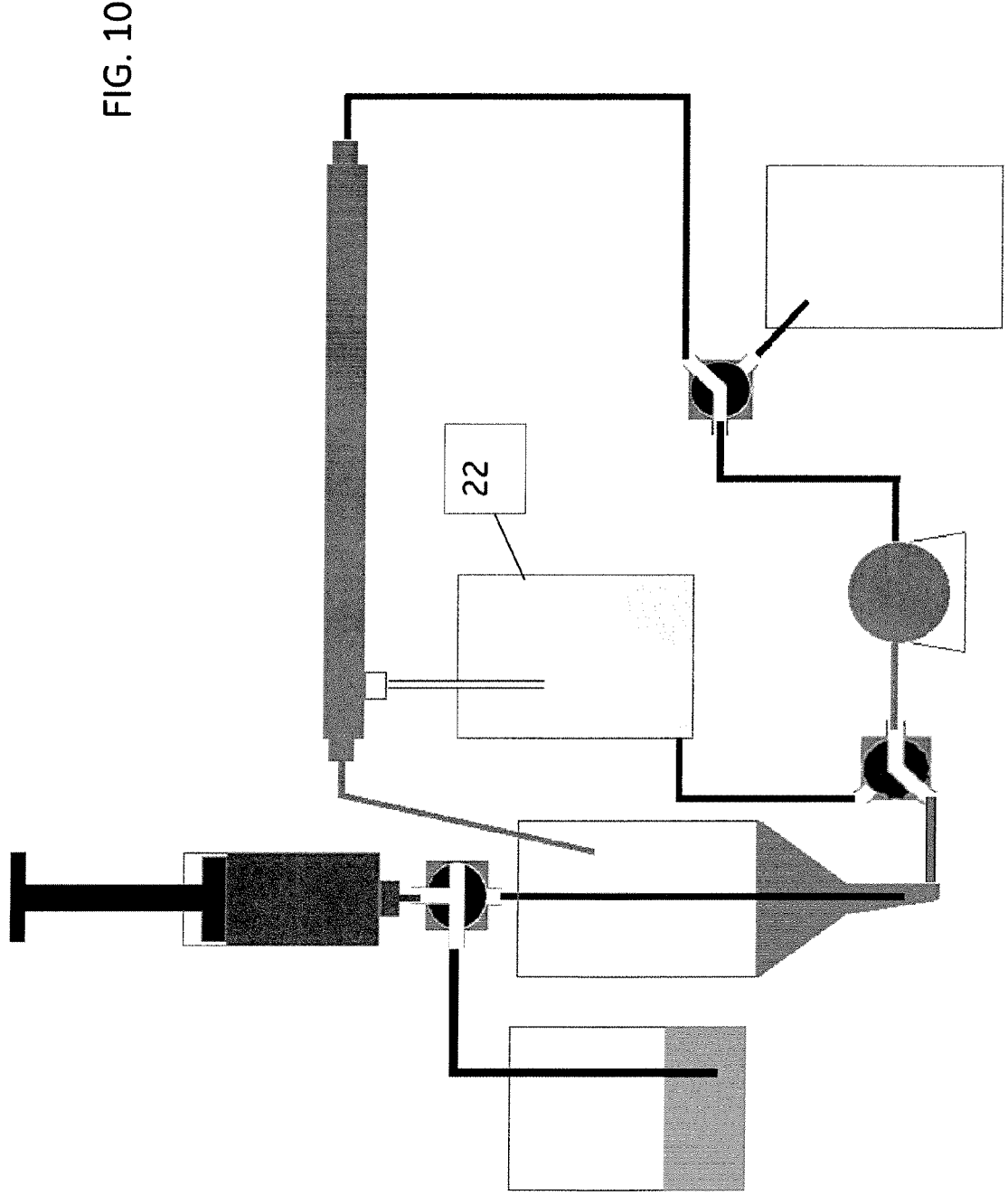
FIG. 10 is a schematic drawing of the embodiment shown in FIG. 9 showing the filter waste being collected in a waste filtration receptacle and the sample recirculating through the system.

FIG. 9 is a schematic drawing of the embodiment shown in FIG. 8 showing pump valve 28 between the vessel and pump 26 in an open position and the mixture flowing through the system from vessel 12 through conduit 18 to filtration device 20. As the mixture is filtered through filtration device 20, the filter waste, which in this example is plasma, is collected in waste filtration receptacle 22 as shown in FIG. 10. The system may be configured to continue recirculating the sample that passes through filtration device 20 until the volume of the sample recirculating through vessel 12 reaches a predetermined level. For example, a sensor may be used to optically monitor the concentration level of total nucleated cells (TNC) in vessel 12.

Figure 11:
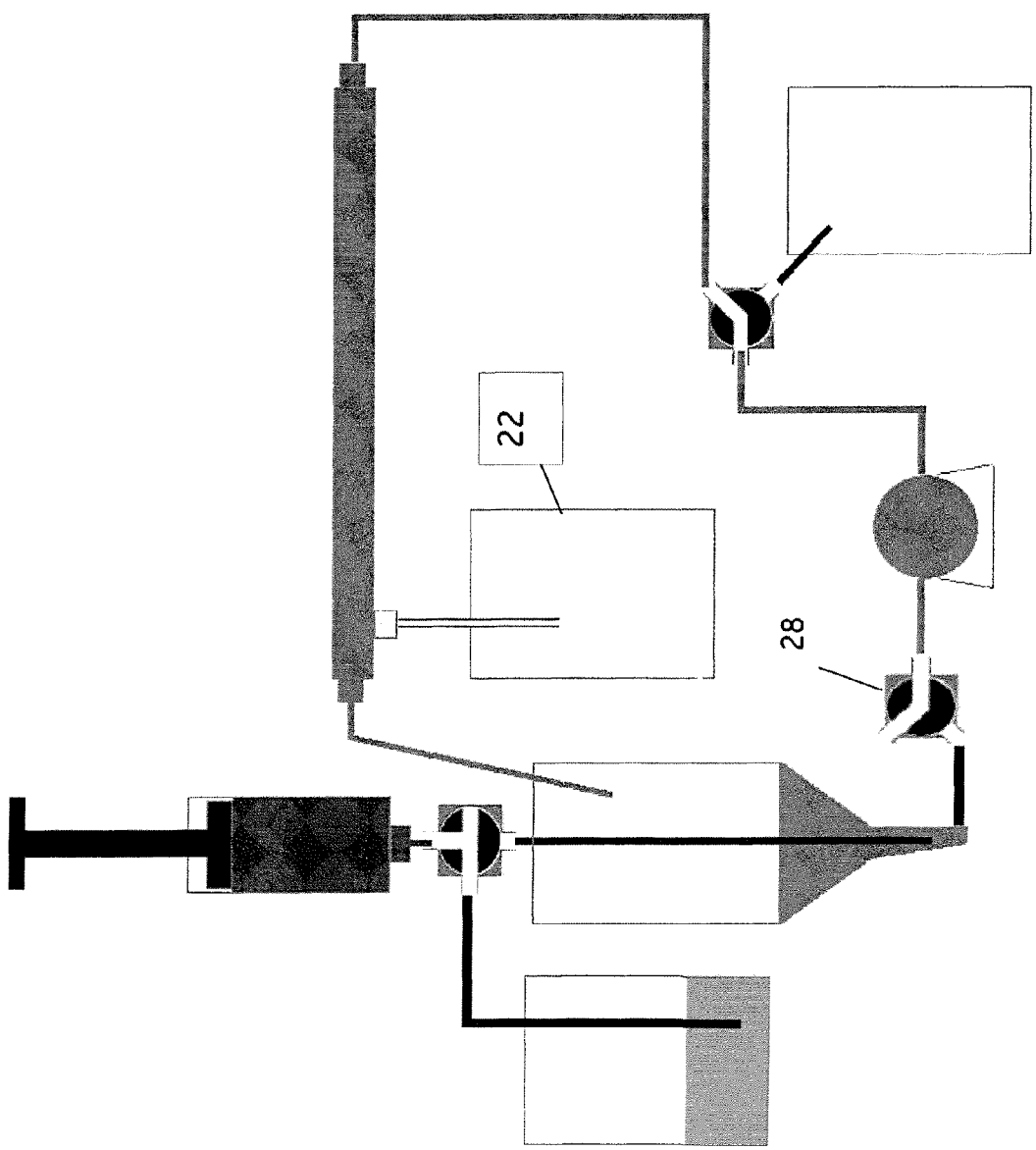
FIG. 11 is a schematic drawing of the embodiment shown in FIG. 10 showing the pump inlet valve in a closed position relative to the vessel and in an open position relative to the waste filtration receptacle and the waste filtrate recirculating through the conduit and filtration device.
Figure 12:
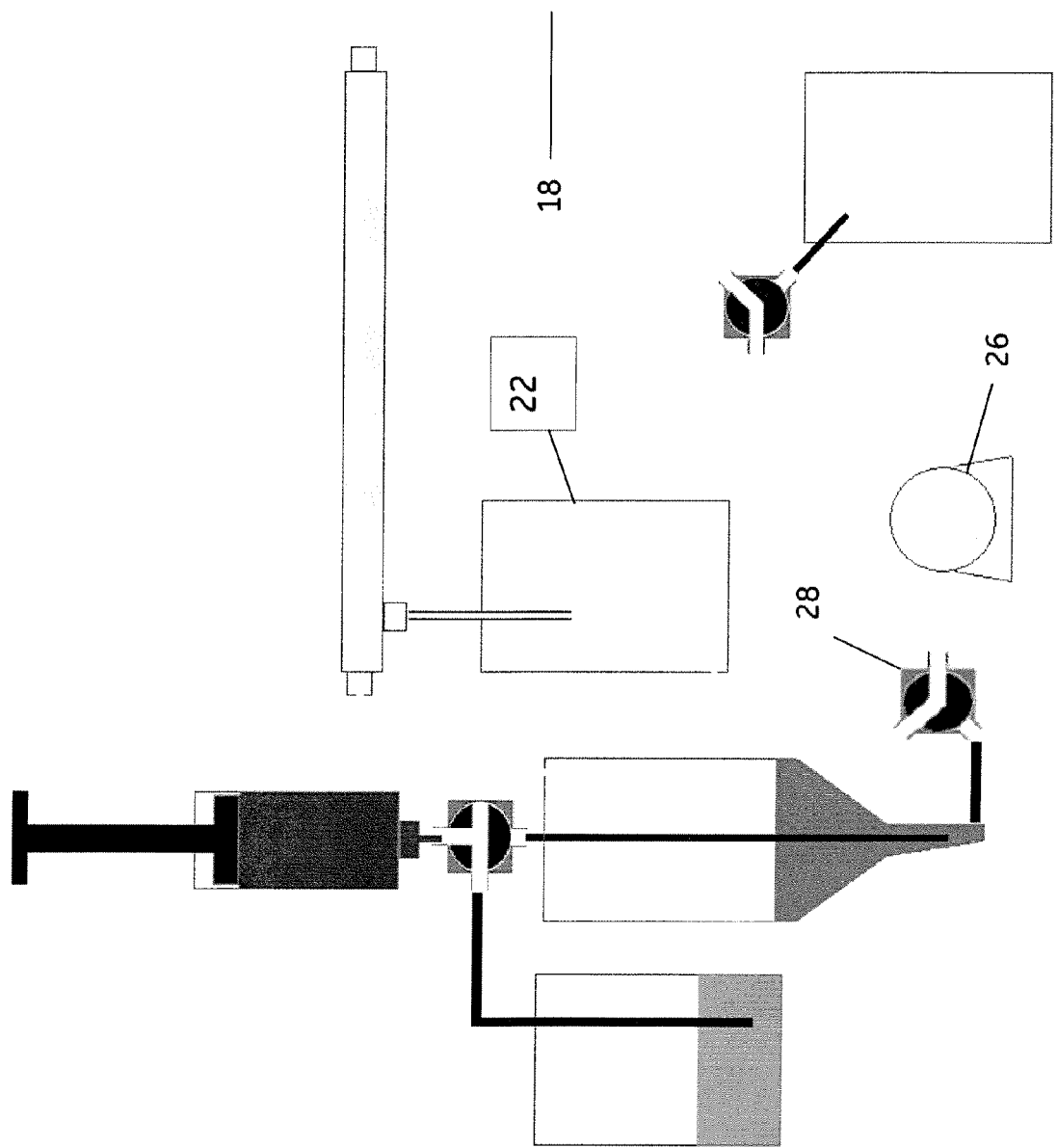
FIG. 12 is a schematic drawing of the embodiment shown in FIG. 11 showing the waste filtrate pumped through the system until it has replaced a target retentate trapped in the fluid path.

To clear filtration device 16, pump inlet valve 28 is closed relative to the vessel and opened relative to waste filtration receptacle 22 to allow the waste filtrate (plasma in this example) to recirculating through conduit 18 and filtration device 20 (FIG. 11). FIG. 12 is a schematic drawing of system 10 shown in FIG. 11 showing the waste filtrate pumped through the system until it has replaced a target retentate (e.g. TNCs) trapped in the fluid path.

The target retentate comprises one or more of the submaterials that intended to be separated from the biological material and collected in target retentate receptacle 24. In this example, the target retentate comprises TNC. Target retentate receptacle may be any receptacle suited for a given purposes such as collection bags for the various blood components. There may be a plurality of waste and target retentate receptacles depending on the materials being processed. Alternatively or in addition to a plurality of receptacles, the waste and target retentate receptacles may be interchangeable from one process to another and even during a single processing session when there are more than one submaterials that are desired to be collected. The system may also comprise a series of filtration devices and waste and target retentate receptacles, to capture and sort varying types of submaterials within a given starting material.

Figure 13:
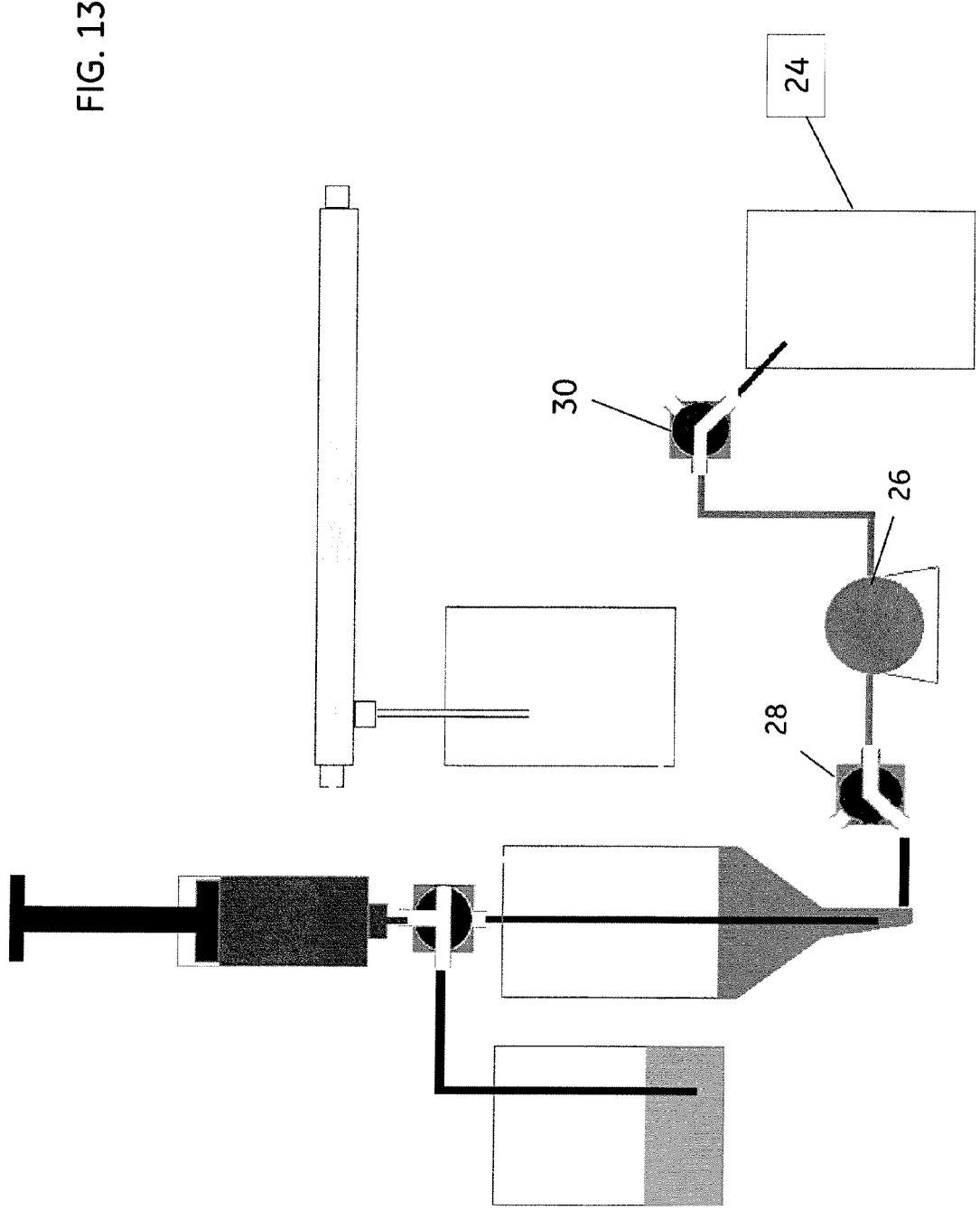
FIG. 13 is a schematic drawing of the embodiment shown in FIG. 12 showing the pump inlet valve in a closed position relative to the waste filtrate receptacle and in an open position relative to the vessel, and a pump outlet valve, between the pump and a target retentate receptacle, in an open position.
Figure 14:
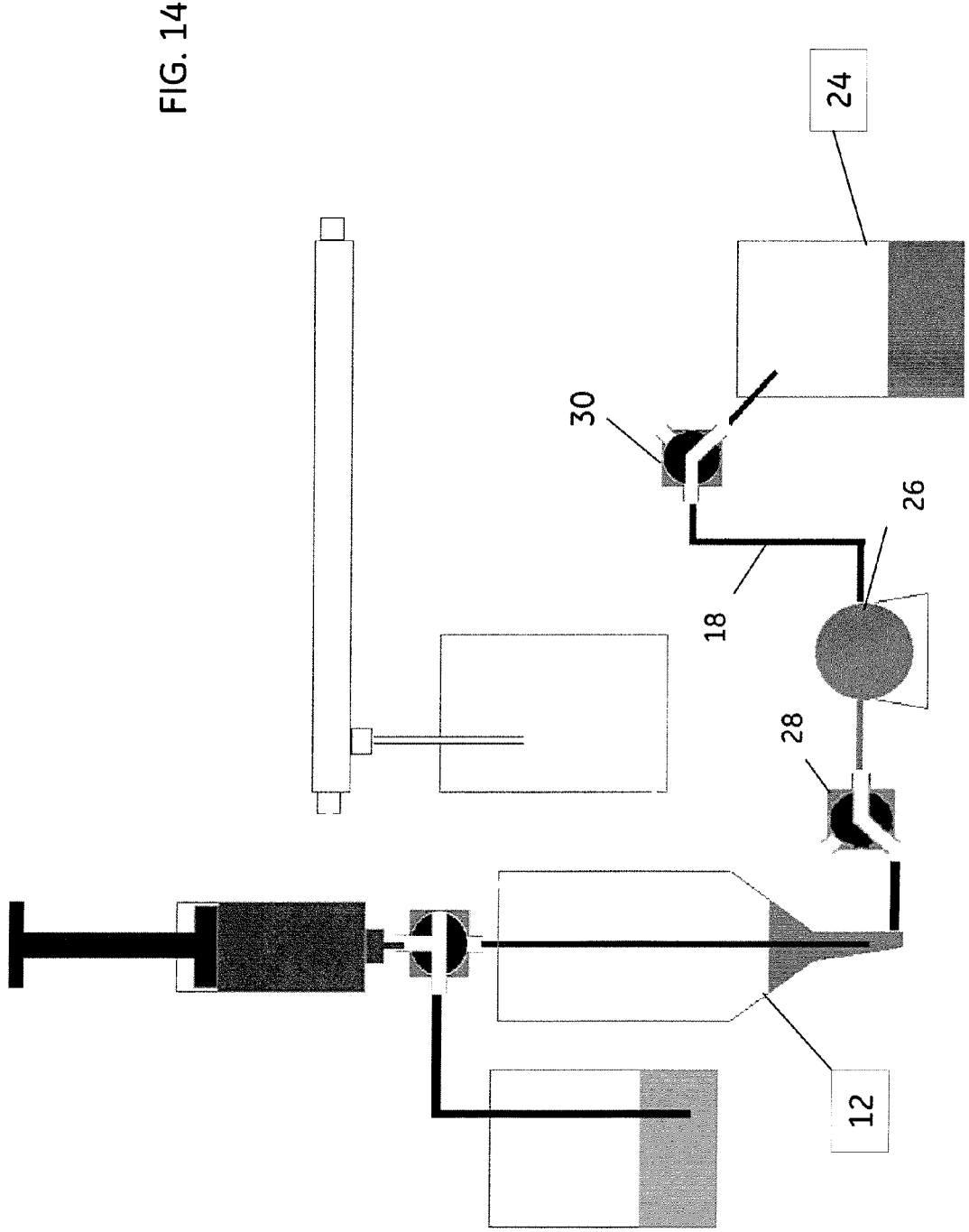
FIG. 14 is a schematic drawing of the embodiment shown in FIG. 13 showing the target retentate being collected in the target retentate receptacle.

FIG. 13 shows system 10 following the step shown in FIG. 12, showing pump inlet valve 28 in a closed position relative to the waste filtrate receptacle and in an open position relative to the vessel, and pump outlet valve 30, between the pump and a target retentate receptacle, in an open position so that the target retentate is collected in the target retentate receptacle as shown in FIG. 14.

Figure 15:
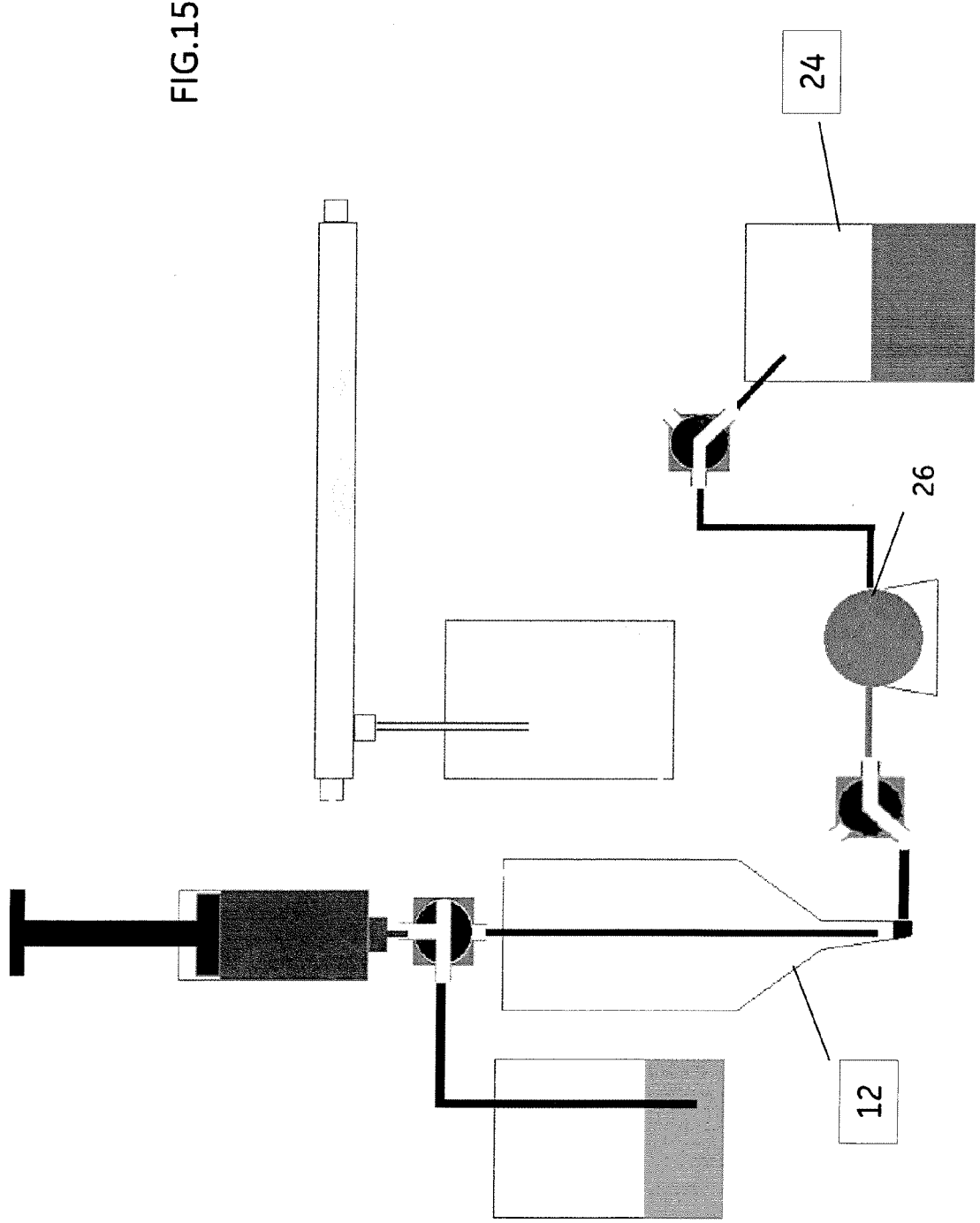
FIG. 15 is a schematic drawing of the embodiment shown in FIG. 14 showing the remaining amount of the target retentate at the bottom of vessel being transported to the target retentate receptacle.
Figure 16:
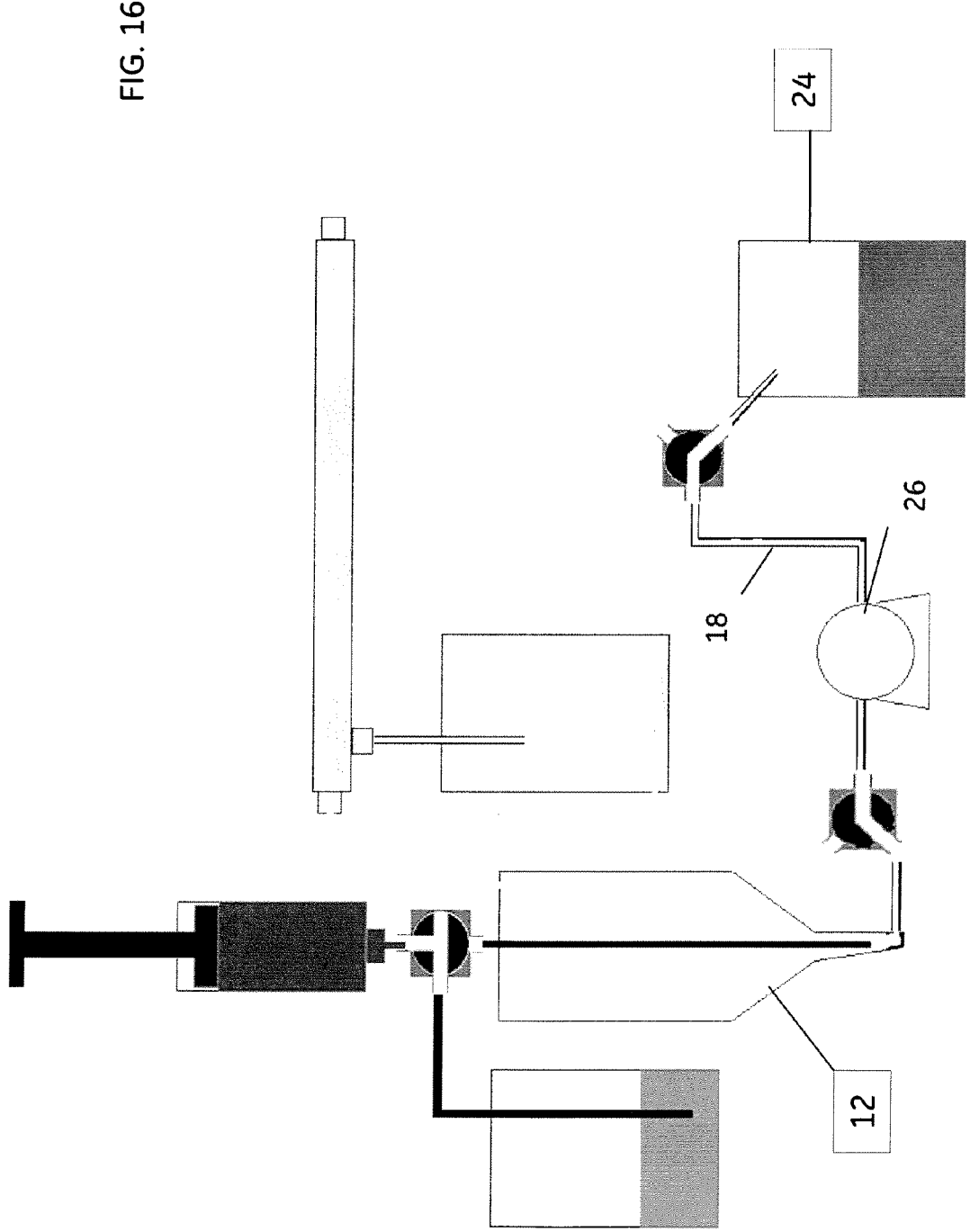
FIG. 16 is a schematic drawing of the embodiment shown in FIG. 15 showing a residual amount of target retentate in the conduit between the vessel land the target retentate receptacle.
Figure 17:
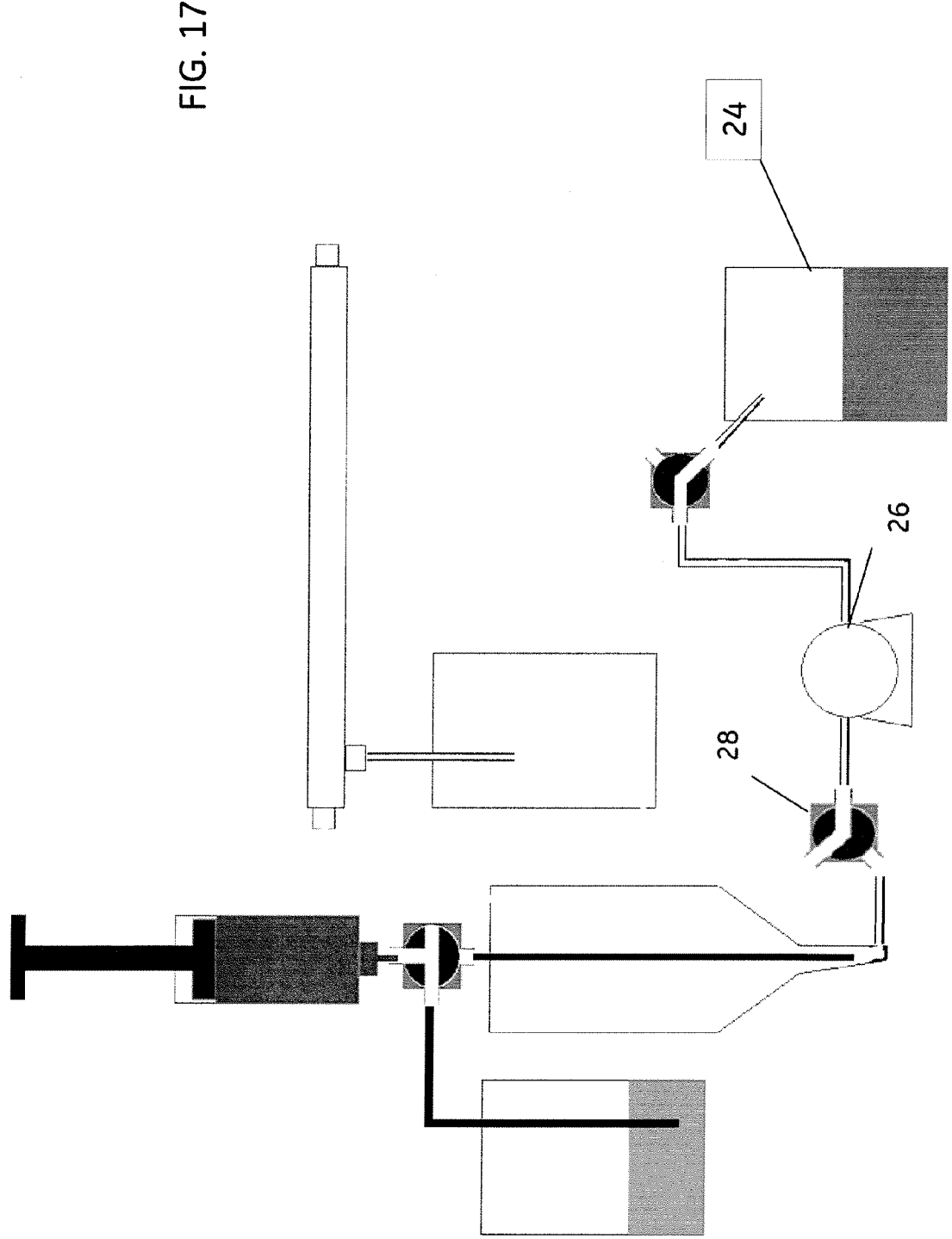
FIG. 17 is a schematic drawing of the embodiment shown in FIG. 16 showing the pump inlet value in an open position relative to the waste filtrate receptacle.
Figure 18:
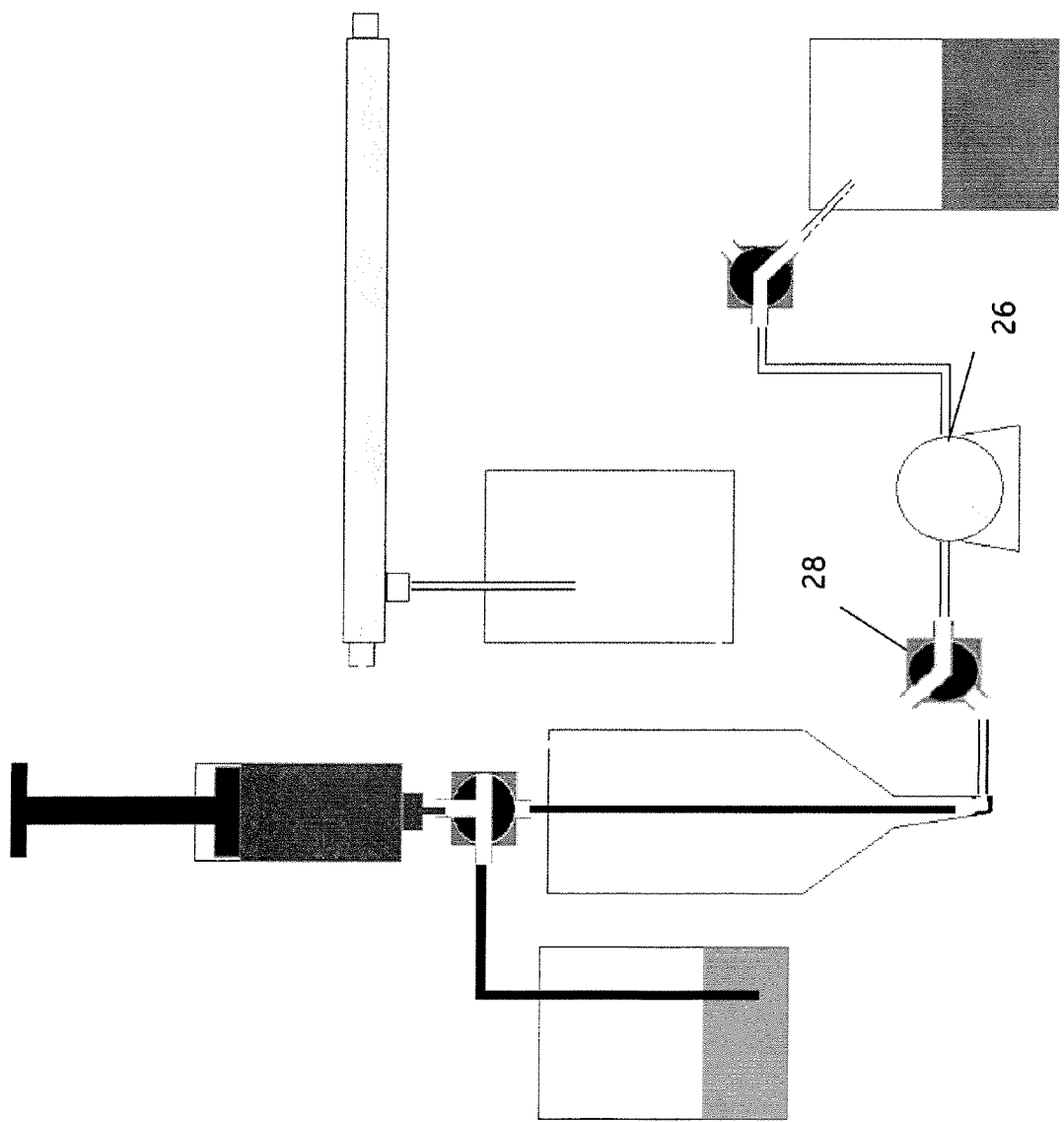
FIG. 18 is a schematic drawing of the embodiment shown in FIG. 17 showing the waste filtrate being transported through the conduit until the waste filtrate has pushed the residual target retentate in the conduit into the target retentate receptacle.

As shown in FIG. 15, even the small remaining amount of the target retentate at the bottom of vessel can be transported to the target retentate receptacle. However, a residual amount of target retentate may remain in the conduit between the vessel and the target retentate receptacle as shown in FIG. 16. To flush and collect this residual target retentate in the conduit, pump inlet valve 28 is opened relative to the waste filtrate receptacle (FIG. 17) to allow the waste filtrate to be pumped through conduit 18 until the waste filtrate has pushed the residual target retentate in the conduit into the target retentate receptacle (FIG. 18).

Figure 19:
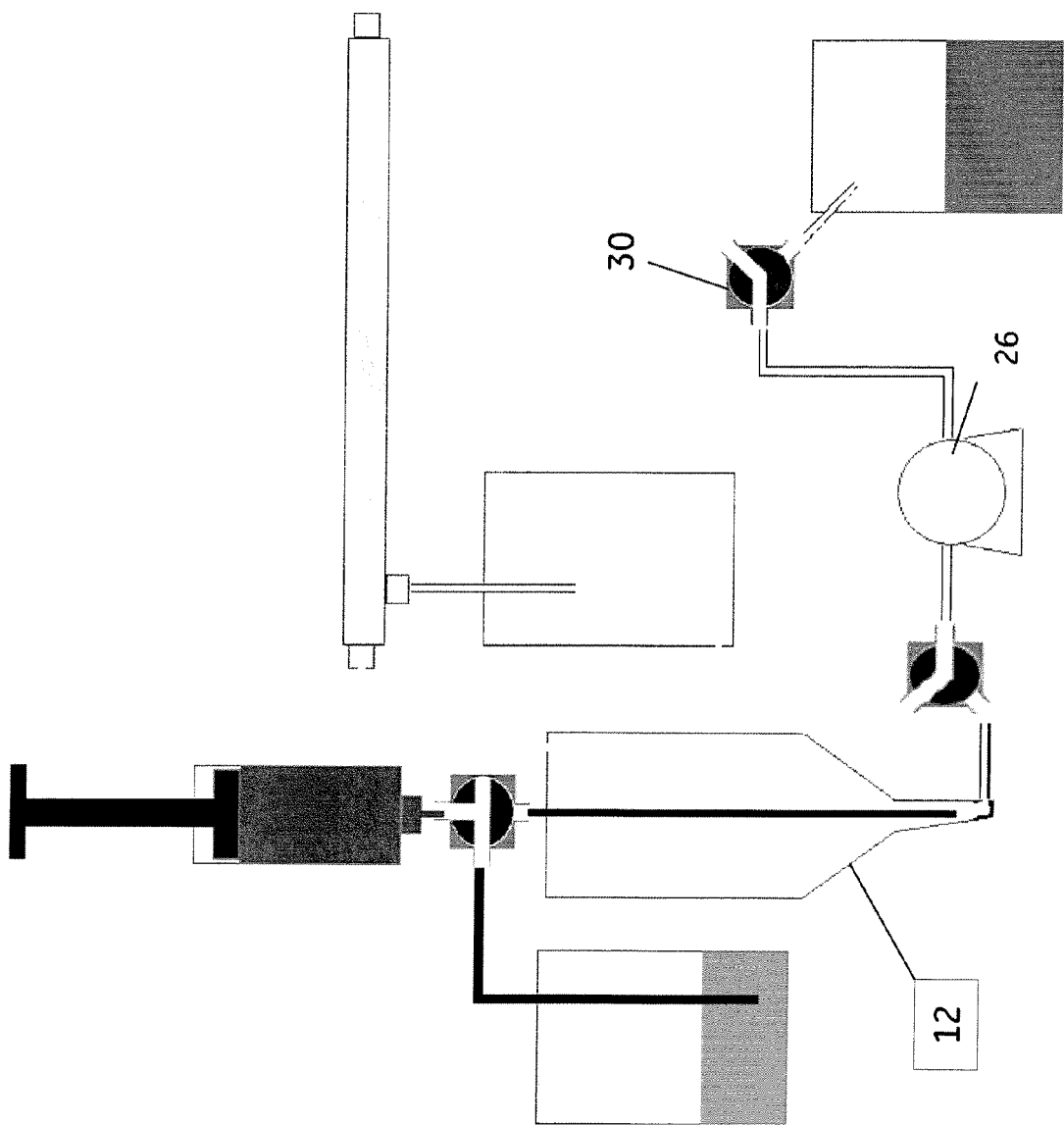
FIG. 19 is a schematic drawing of the embodiment shown in FIG. 18 showing the pump outlet value in a closed position relative to the target retentate receptacle and the waste filtrate being transported to the vessel.
Figure 20:
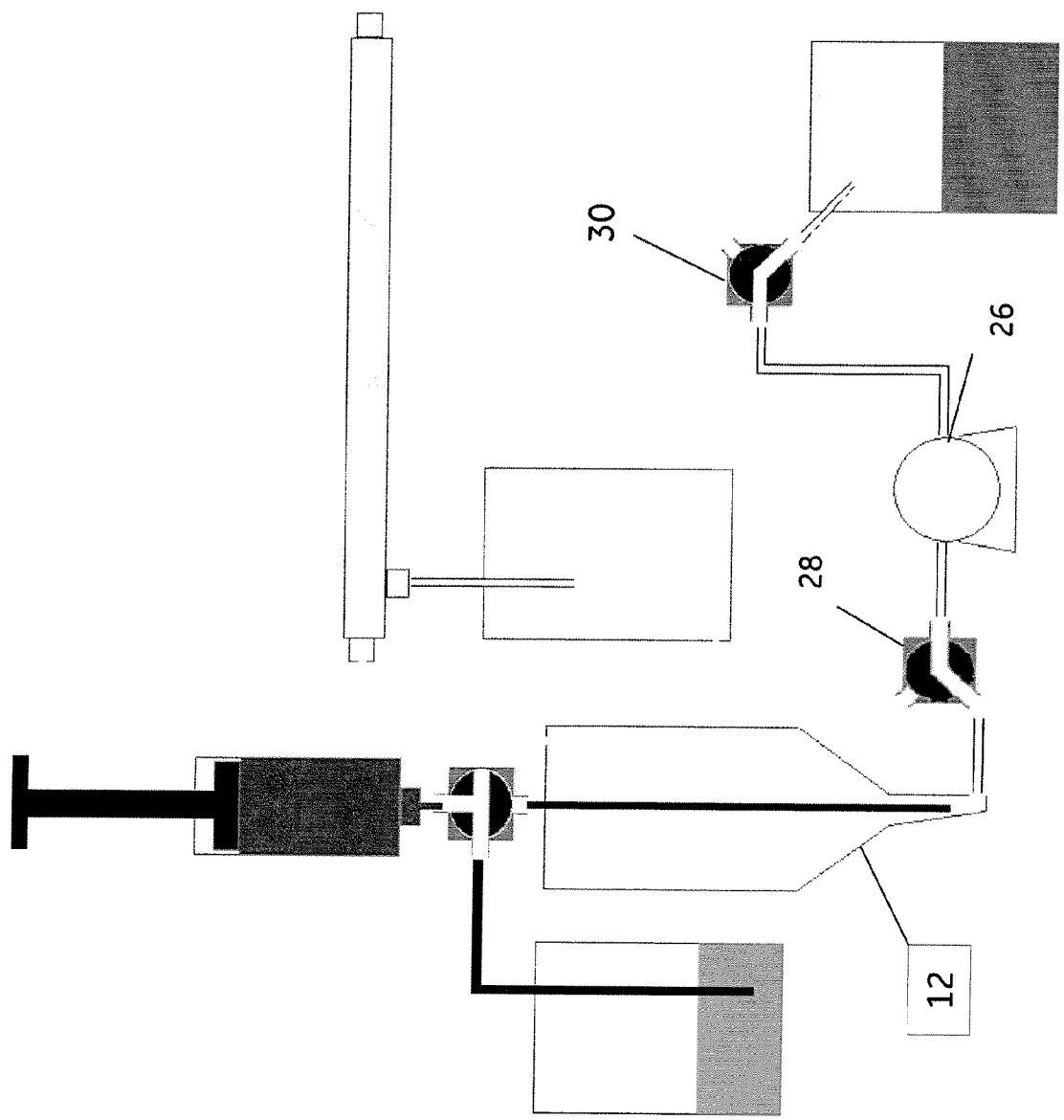
FIG. 20 is a schematic drawing of the embodiment shown in FIG. 19 showing the waste filtrate and any remaining target retentate in the system being collected in an auxiliary filtrate receptacle.

As a final flush of the system, the waste filtrate (e.g. plasma) may be flush through the system. As shown in FIG. 19, the pump outlet valve is closed relative to the target retentate receptacle and the waste filtrate is pumped through the system to flush out the entire system and to collect any remaining submaterials in the vessel. This collection of submaterials in the vessel may then be collected in an auxiliary filtrate receptacle that is interchangeable, or in addition to, target retentate receptacle 24 (FIG. 20).

The filtration device of the system shown in FIG. 1 is capable of isolating a cell fraction from a complex biological fluid such as peripheral blood, cord blood, and/or bone marrow. An example of a method for making the filtration device of system 10 is provided below.

System 10 may comprise other auxiliary components such as a memory storage device for storing information and data about the various materials, submaterials, and agents that may be processed through the system, and information about the mechanical and environmental variables to which the system may be adapted. The system may be programmed to intuitively adjust the mechanics and conditions of a given process in response to information and data collected by the sensors of the system. The memory storage device may comprise any suitable hard drive memory associated with the processor such as the ROM (read only memory), RAM (random access memory) or DRAM (dynamic random access memory) of a CPU (central processing unit), or any suitable disk drive memory device such as a DVD or CD, or a zip drive or memory card or stick. The memory storage device may be remotely located from the system and yet still be accessed through any suitable connection device or communications network including but not limited to local area networks, cable networks, satellite networks, and the Internet, regardless whether hard wired or wireless. The processor or CPU may comprise a microprocessor, microcontroller and a digital signal processor (DSP).

The system may further comprise an entry device and a display device to enable a user to input information into the system and to access and display information and data about a given process run or a plurality of runs, to compile information and data, and/or to generate reports. The display device may comprise any suitable device capable of displaying a digital image such as, but not limited to, devices that incorporate an LCD or CRT.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system having a fluid flow path for processing biological material comprising red blood cells and nucleated cells, comprising:
   A vessel for containing and enabling the biological material to separate into two or more distinct layers of submaterials, wherein one of the distinct layers of submaterials comprises a layer of red blood cells;
   An extraction device configured to remove the layer of red blood cells from the vessel, wherein the extraction device comprises a pick up line having a distal end located within the vessel at a level at which the layer of red blood cells settles during operation;
   A filtration device, located downstream along the fluid flow path from the extraction device, for separating the nucleated cells from the remaining submaterials;
   A valve located between the vessel and the filtration device;
   A conduit through which one or more submaterials are transported between the vessel and the filtration device; and
   A control device configured to automatically initiate the extraction device to remove the layer of red blood cells from the vessel and after removal of the red blood cells, to automatically open the valve to transport one or more of the submaterials remaining in the vessel further downstream along the fluid flow path to the filtration device via the conduit.

2. The system of claim 1, further comprising one or more receptacles for at least temporarily storing one or more filtrates.

3. The system of claim 2, wherein one of the receptacles is a waste filtrate receptacle.

4. The system of claim 2, wherein one of the receptacles is a target retentate receptacle.

5. The system of claim 1, further comprising a pump, in fluid communication with the conduit, for facilitating the transport of one or more submaterials between the vessel and the filtration device.

6. The system of claim 5, further comprising a receptacle for at least temporarily storing a target retentate.

7. The system of claim 6, further comprising a receptacle for at least temporarily storing a waste filtrate.

8. The system of claim 7, further comprising a valve along the conduit for selectively directing target retentate into the target retentate receptacle.

9. The system of claim 7, further comprising a valve along the conduit for selectively recirculating the waste filtrate at least partially through the conduit.

10. The system of claim 1, wherein the vessel is adapted to separate the material into submaterials at least in part based on the relative weight of two or more submaterials.

11. The system of claim 10, wherein the vessel is adapted to separate the submaterials into sedimentary layers.

12. The system of claim 11, wherein the extraction device is adapted to draw off one or more of the sedimentary layers.

13. The system of claim 1, wherein the extraction device is adapted to draw off a lowermost layer within the vessel, wherein the lowermost layer is substantially red blood cells.

14. The system of claim 12, wherein the extraction device is adapted to draw off an uppermost layer within the vessel.

15. The system of claim 1, further comprising a valve, in fluid communication with an agent receptacle, to selectively remove a determined amount of agent from the agent receptacle and introduce the determined amount of agent into the vessel.

16. The system of claim 15, wherein the extraction device is further adapted to draw a determined amount of material from the vessel, into which the agent has previously been introduced, and then return the drawn material back into the vessel, to facilitate mixing of the material with the agent.

17. The system of claim 1, further comprising a sensing device for determining level of the red blood cells in the vessel.

18. The system of claim 1, wherein the transportation of one or more of the submaterials between the vessel and the filtration device is automated.

19. The system of claim 1, further comprising a sensor that determines the presence of one or more of the submaterials in the vessel.

* * * * *